(12) United States Patent
Cabri et al.

(10) Patent No.: US 9,206,133 B2
(45) Date of Patent: Dec. 8, 2015

(54) PROCESS FOR THE SYNTHESIS OF 7-CHLORO-4-(PIPERAZIN-1-YL)-QUINOLINE

(75) Inventors: Walter Cabri, Rozzano (IT); Roberto Castagnani, Sezze Scalo (IT); Silvia Armaroli, Gallo Poggio Renatico (IT); Gianandrea Quattrociocchi, Veroli (IT); Vincenzo Colangeli, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 14/123,893

(22) PCT Filed: Jun. 5, 2012

(86) PCT No.: PCT/EP2012/060553
§ 371 (c)(1),
(2), (4) Date: Feb. 12, 2014

(87) PCT Pub. No.: WO2012/168213
PCT Pub. Date: Dec. 13, 2012

(65) Prior Publication Data
US 2014/0200346 A1    Jul. 17, 2014

(30) Foreign Application Priority Data
Jun. 6, 2011    (EP) .................................. 11168792

(51) Int. Cl.
C07D 401/04    (2006.01)
C07D 215/46    (2006.01)

(52) U.S. Cl.
CPC .................... C07D 215/46 (2013.01)

(58) Field of Classification Search
CPC .................................................. C07D 401/04
USPC ....................................................... 544/363
See application file for complete search history.

(56) References Cited

U.S. PATENT DOCUMENTS

| | | |
|---|---|---|
| 3,173,918 A | 3/1965 | Baget et al. |
| 3,331,843 A | 7/1967 | Tomcufcik et al. |
| 2006/0270852 A1 | 11/2006 | Yadav et al. |

FOREIGN PATENT DOCUMENTS

| | | | |
|---|---|---|---|
| CN | 101440063 B | | 7/2011 |
| IN | 639/MUM/2005 | | 9/2005 |
| WO | WO 2004/002960 | * | 1/2004 |
| WO | WO 2009/050734 A2 | | 4/2009 |

OTHER PUBLICATIONS

Matsuno et al. (J. Med. Chem. 2003, 46, 4910-4925).*
Sundru et al. (Bioorganic & Medicinal Chemistry 17 (2009) 6451-6462).*
Bavin, M., "Polymorphism in Process Development," *Chem. Ind.* 21:527-529, Society of Chemical Industry, London, United Kingdom (1989).
Braga, D. et al., "Crystal polymorphism and Multiple Crystal Forms," *Struct. Bond* 132:25-50, Springer-Verlag, Berlin, Germany (2009).
Brittain et al., "Polymorphism in Pharmaceutical Solids Passage," *Polymorphism in Pharmaceutical Solids*:235-238, Taylor & Francis, London, United Kingdom (1999).
Caira, M.R., "Crystalline Polymorphism of Organic Compounds," *Top. Curr. Chem.* 198:163-208, Springer Verlag, Berlin, Germany (1998).
Cheronis, N.D., ed., "Purification of Solids by Crystallization," in *Semimicro Experimental Organic Chemistry*, pp. 31-49, Hadrian Press, Inc., United States (1958).
International Search Report for International Appl. No. PCT/EP2012/060553, European Patent Office, Rijswijk, Netherlands, mailed Jan. 17, 2013.
Liu, Y. et al., "Discovery of a Novel CCR5 Antagonist Lead Compound Through Fragment Assembly," *Molecules* 13:2426-2441, MDPI, Basel, Switzerland (2008).
Singh, T. et al., "Antimalarials 7-Chloro-4-(substituted amino)quinolones," *J. Med. Chem.* 14:283-286, American Chemical Society (1971).
Vennerstrom, J.L. et al., "Bisquinolines. 2. Antimalarial N,N-Bis(7-chloroquinolin-4-yl)heteroalkanediamines," *J. Med. Chem.* 41:4360-4364, American Chemical Society (1998).
Morissette, S.L. et al., "High-throughput crystallization: polymorphs, salts, co-crystals and solvates of pharmaceutical solids," *Adv. Drug Deliv. Rev.* 56:275-300, Elsevier B.V., Netherlands (2004).

* cited by examiner

*Primary Examiner* — Bruck Kifle
(74) *Attorney, Agent, or Firm* — Sterne, Kessler, Goldstein & Fox P.L.L.C.

(57) ABSTRACT

The present invention provides a new process of synthesis of a polymorph of 7-chloro-4-(piperazin-1-yl)-quinoline of Formula I. Said quinoline compound is substantially pure of any impurities. The present invention further provides the use of the above-mentioned polymorph of 7-chloro-4-(piperazin-1-yl)-quinoline in the synthesis of piperaquine or one of its pharmaceutically acceptable salts.

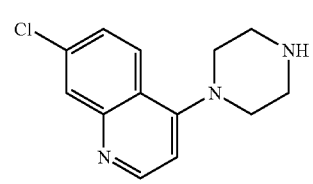

(I)

8 Claims, 4 Drawing Sheets

Figure 6

| Form A | | Form B | | Form C | | Form D | | Form E | |
|---|---|---|---|---|---|---|---|---|---|
| 2θ | % Relative Intensity | 2θ | % Relative Intensity | 2θ | % Relative Intensity | 2θ | % Relative Intensity | 2θ | % Relative Intensity |
| 20.4 | 100 | 6.95 | 100 | 23.6 | 100 | 18.1 | 100 | 20.6 | 100 |
| 23.1 | 88.1 | 20.4 | 76.9 | 23.95 | 79.5 | 19.8 | 64.3 | 27.6 | 35.4 |
| 18.2 | 38.7 | 25.8 | 68.3 | 20.4 | 60.7 | 16.45 | 61.8 | 24.2 | 29 |
| 24.7 | 38.3 | 10.3 | 53.5 | 23.2 | 59 | 17.85 | 60 | 30.2 | 28.5 |
| 26.3 | 25.9 | 13.7 | 39.7 | 24.45 | 54.9 | 23.1 | 59 | 24.5 | 27.7 |
| 12.1 | 21.9 | 12.35 | 39.1 | 18.3 | 52.5 | 24.65 | 57.2 | 14.4 | 23.3 |
| 27.9 | 21.3 | 25.25 | 32 | 18.6 | 49.2 | 20.35 | 54.8 | 24.8 | 21.6 |
| 16.8 | 17.9 | 29.05 | 32 | 24.7 | 48.4 | 27.65 | 54.8 | 23.2 | 18.4 |
| 16.5 | 17.0 | 22.85 | 29.8 | 22.2 | 38.5 | 8.05 | 45.2 | 11.65 | 15 |
| 30.0 | 16.8 | 17.9 | 23.4 | 25.75 | 29.5 | 13.5 | 44.6 | 28.65 | 14.6 |
| 19.5 | 16.5 | 24.6 | 23.1 | 22.5 | 28.7 | 8.25 | 43.6 | 12.2 | 13.2 |
| 30.2 | 15.9 | 28.5 | 19.4 | 26.3 | 23.4 | 24.25 | 36.3 | | |
| 19.9 | 14.2 | 28.85 | 18.5 | 14.75 | 22.9 | 12.05 | 35.4 | | |
| | | | | 15.25 | 22.9 | 24.05 | 30.9 | | |
| | | | | 27.6 | 22.9 | | | | |
| | | | | 28.55 | 22.9 | | | | |
| | | | | 31.1 | 22.9 | | | | |
| | | | | 28.05 | 22.1 | | | | |

PROCESS FOR THE SYNTHESIS OF 7-CHLORO-4-(PIPERAZIN-1-YL)-QUINOLINE

FIELD OF THE INVENTION

The present invention relates to a new process of synthesis of 7-chloro-4-(piperazin-1-yl)-quinoline, a key intermediate in the synthesis of piperaquine. The invention further relates to the crystalline form of said quinoline derivative and to its use in the synthesis of piperaquine itself.

BACKGROUND OF THE INVENTION

Piperaquine (1,3-bis-[4-(7-chloroquinolyl-4)-piperazin-1]-propane) of Formula 1 is an anti-malarial product that belongs to the bisquinoline class of chemical compounds.

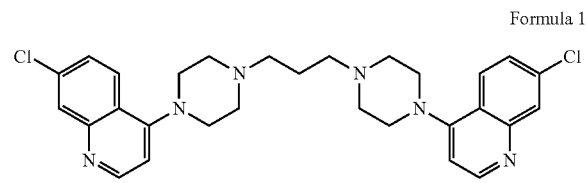 [SMILES: Clc1ccc2c(N3CCN(CCCN4CCN(c5ccnc6cc(Cl)ccc56)CC4)CC3)ccnc2c1]

Formula 1

Piperaquine was first synthesized in 1960s (U.S. Pat. No. 3,173,918) and was used in therapy in China and Vietnam. In the last decade it has been object of renewed interest as one of a number of compounds suitable for Artemisinin-based Combination Therapy (ACT). Eurartesim® contains a fixed-ratio drug combination between piperaquine phosphate and dihydroartemisinin to treat uncomplicated P. falciparum malaria. Since piperaquine presents an extremely long half-life, its combination is expected to be effective both in treating clinical malaria and in giving protection from re-infection.

Even if various processes for the synthesis of piperaquine have been described in the literature, they usually involve the use of the key intermediate piperazine quinoline of Formula I, which synthesis is depicted underneath (Scheme 1).

Scheme 1

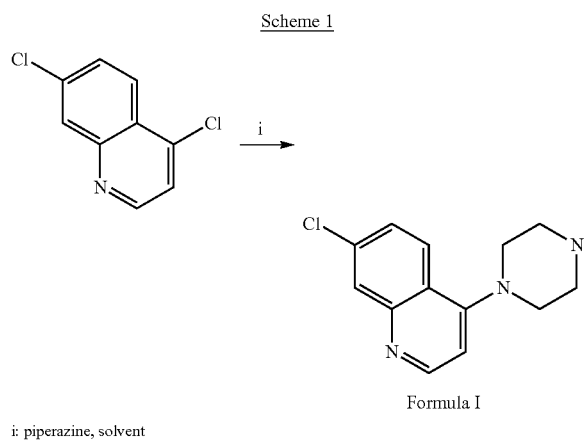

Formula I i: piperazine, solvent

Most of the synthetic routes toward 7-chloro-4-piperazin-1-yl-quinoline that have been devised mainly diverge by the reaction conditions used (i.e., type of solvent, reaction temperature, work-up conditions), purity of this intermediate, rather than by the choice of the reagents themselves. A further common point to most of these syntheses resides in the difficulty to purify this key intermediate of Formula I from side-product or excess of piperazine, resulting in low quality of final piperaquine. Indeed, the main drawback identified when reacting the 4,7-dichloroquinoline with piperazine is the concomitant formation of a dimer of Formula 2.

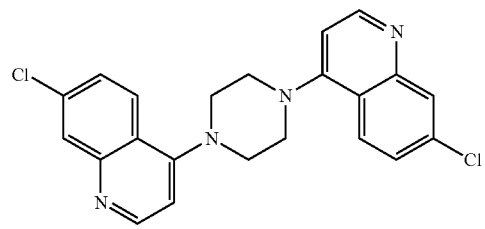

Formula 2

Such a side-product has been reported to possess some toxicity (Singh T., et al., J. Med. Chem., 1971, 14, 4, 283).

Moreover, lots of existing syntheses of compounds of Formula I require elevated reaction mixture temperatures, and/or toxic solvents, and/or laborious extraction processes, and/or highly diluted reaction conditions, and/or large excess of piperazine which at the end results difficult to completely remove.

The synthesis of 7-chloro-4-(piperazin-1-yl)-quinoline was first disclosed more than 40 years ago (U.S. Pat. No. 3,331,843). The reaction between 4,7-dichloroquinoline and four equivalents of anhydrous piperazine involved the use of phenol as solvent and a laborious work-up to obtain the desired adduct. The latter required a further purification to ensure a high quality final compound presenting a melting point equal to 113.5-114.5° C. corresponding to the one of the pure derivative. Furthermore, the relatively high dilution of the reaction coupled to the nocuous character of the solvent (i.e., phenol) do not render this synthesis really practicable on large scale. Singh T., et al., reported a synthesis of 7-chloro-4-(piperazin-1-yl)-quinoline involving a 10 M excess of piperazine, the reaction being conducted at reflux in ethoxyethanol for 24 h. The work-up involved basification by means of NaOH and a crystallization from cyclohexane (Singh T., et al., J. Med. Chem., 1971, 14, 4, 283). However, the toxicity of this solvent renders this synthesis rather inadequate.

Vennerstrom J. L., et al. a synthesis that involved distillation of the solvent and of the excess of piperazine prior to an extraction with a ternary mixture of ethyl acetate-diethyl-ether-dichloromethane. The crude reaction mixture was then recrystallized from diethylether to get the desired adduct (Vennerstrom J. L., et al., J. Med. Chem. 1998, 41, 4360).

Liu Y., et al., reported lately a further synthesis of 7-chloro-4-(piperazin-1-yl)-quinoline involving highly diluted conditions in N-methyl-2-pyrrolidinone and a work-up by means of dichloromethane to afford the desired compound in 54% yield (Liu Y., et al., Molecules, 2008, 13, 2426).

WO04002960 reported a 65% yielding synthesis of 7-chloro-4-(piperazin-1-yl)-quinoline which made use of ten equivalents of piperazine and high ethanolic dilution conditions, the reaction being conducted in sealed-tube.

In patent application 639MUM2005, the Applicant reported a synthesis implying high methanolic dilution conditions coupled to a work-up necessitating a cooling to 10° C. of the reaction mixture prior to filtrate off the precipitated dimer impurity as well as the excess of piperazine used. The desired adduct was then extracted by means of dichloromethane to give rise to a 98% pure compound. It is noteworthy that even after a filtration step and extraction with dichloromethane, the purity of the compound is only 98%. A higher purity could be obtained by means of a laborious successive crystallization step.

U.S. Ser. No. 11/420,400 (corresponding to patent application US2006/270852) reported a synthesis wherein 7-chloro-4-(piperazin-1-yl)-quinoline was prepared in 95% yield after a long 36 hour period in refluxing i-propyl alcohol in the presence of potassium carbonate.

Sunduru, N., et al., disclosed lately a synthesis wherein 7-chloro-4-(piperazin-1-yl)-quinoline was prepared in 80% yield after 5 hours at reflux in MeOH in the presence of 5 equivalents of piperazine. Surprisingly, the melting point of the obtained adduct (mp=160-162° C.) diverges by more than 50° C. with respect to the one reported elsewhere (Sunduru N., et al., *Bioorg. Med. Chem.*, 2009, 17, 6451).

WO09050734 reported a synthesis wherein 7-chloro-4-(piperazin-1-yl)-quinoline was prepared in 82 to 86% yield from heating to reflux in i-PrOH a 3/1 mixture of piperazine and 4,7-dichloroquinoline in the presence of potassium carbonate. Such a process further involved extraction of the aqueous phase with $CH_2Cl_2$ in order to remove the dimer impurity, and subsequent basification of the aqueous phase with liquor ammonia prior to a second extraction with $CH_2Cl_2$. After removal of the solvent, the residue was taken-up in hexane to obtain 7-chloro-4-(piperazin-1-yl)-quinoline in 98.56% purity.

Therefore, devising a new synthesis of the precious 7-chloro-4-(piperazin-1-yl)-quinoline which avoids the use toxic reagents and/or solvent, and/or laborious extraction processes, and/or highly diluted reaction conditions, and/or large excess of piperazine which at the end results difficult to completely remove is highly desirable.

DESCRIPTION OF THE INVENTION

The present invention provides a new "green" process of synthesis of a polymorph of 7-chloro-4-(piperazin-1-yl)-quinoline and the use of the latter in the synthesis of piperaquine or one of its pharmaceutically acceptable salts. Said obtained quinoline compound is substantially pure of any impurities. In particular, the synthesis object of the present invention allows the production of the compound of Formula I the latter being free of any traces of compounds of formula 2 and of any substantial traces of non reacted piperazine.

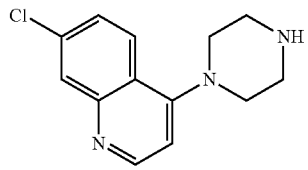

Formula I

The synthesis object of the present invention is environment-friendly (green) and easily feasible in large scale conditions and represents a major improvement over the existing syntheses. It is a highly efficient and cost effective way of synthesising Formula I compound.

An embodiment of this invention consists of a process to synthesize the compound of Formula I, by reacting 4,7-dichloroquinoline and piperazine in a methanolic solution. In a preferred embodiment, less than three stoichiometric equivalents of piperazine are added.

In a more preferred embodiment, the reaction mixture is filtered after 8 hours of reflux in methanol.

In an even more preferred embodiment, the compound of Formula I is obtained highly pure by crystallization.

In a further even more preferred embodiment, the crystallization process involves the use of water.

In a further more preferred embodiment, 7-chloro-4-(piperazin-1-yl)-quinoline is obtained in a specific polymorphic Form.

In particular, the polymorphic Forms B, C, and D are preferred.

Even more particularly, polymorphic Form B is especially preferred.

The term "washing" and any derived word, reflect that water is the ingredient involved in the process of washing.

The term "rinsing" and any derived word, reflect that an organic solvent is the ingredient involved in the process of rinsing.

The expression "substantially pure" means that the purity of the compound it refers to is equal to or higher than 99%.

The expression "substantially the same" means that the skilled person will not see any difference between the two objects compared. Particularly, when referred to a X-ray spectra, it means that the two spectra even if not 100% identical, do correspond to the same chemical entity because the picks of each spectra only diverge within the experimental margin with respect to the 2-theta values as well as with the intensity of each pick.

Form B

In a preferred embodiment, crystalline Form B of 7-chloro-4-(piperazin-1-yl)-quinoline is obtained.

According to the present invention there is provided a crystalline Form B of 7-chloro-4-(piperazin-1-yl)-quinoline, which has a X-ray powder diffraction pattern with at least five specific peaks at about 2-theta=6.95°, 20.40°, 25.80°, 10.30° and 13.70° wherein said values may be plus or minus 0.1° 2-theta.

Form C

In a still further preferred embodiment, crystalline Form C of 7-chloro-4-(piperazin-1-yl)-quinoline is obtained.

According to the present invention there is provided a crystalline Form C of 7-chloro-4-(piperazin-1-yl)-quinoline, which has a X-ray powder diffraction pattern with at least nine specific peaks at about 2-theta=23.6°, 23.95°, 20.4°, 23.2°, 24.45°, 18.3°, 18.6°, 24.7°, and 22.2° wherein said values may be plus or minus 0.1° 2-theta.

Form D

In a still further more preferred embodiment, crystalline Form D of 7-chloro-4-(piperazin-1-yl)-quinoline is obtained.

According to the present invention there is provided a crystalline Form D of 7-chloro-4-(piperazin-1-yl)-quinoline, which has a X-ray powder diffraction pattern with at least eight specific peaks at about 2-theta=18.1°, 19.8°, 16.45°, 17.85°, 23.1°, 24.65°, 20.35°, and 27.65° wherein said values may be plus or minus 0.1° 2-theta.

DESCRIPTION OF THE DRAWINGS

FIG. 6: table showing all the peaks of the X-diffraction spectra of the five polymeric forms.

EXAMPLES

Figure 1:
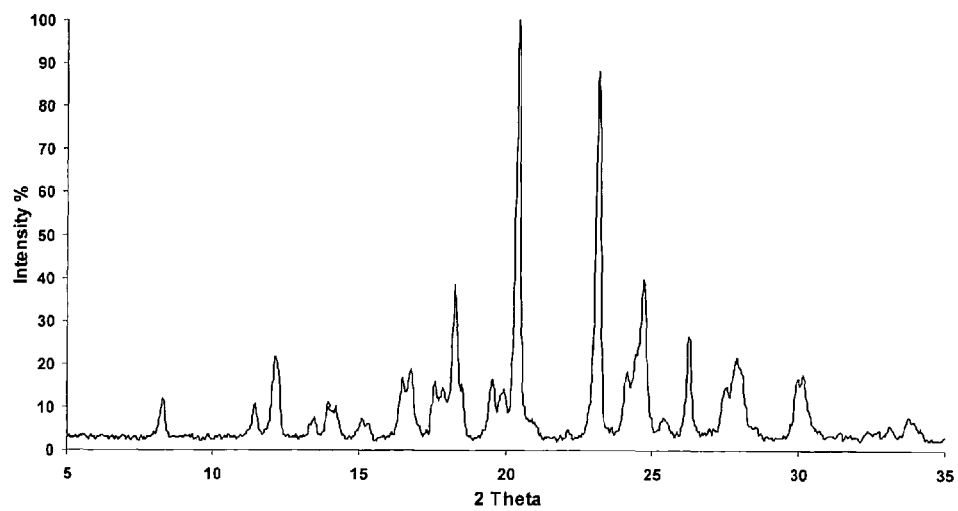
FIG. 1: represents the X-ray spectra of 7-chloro-4-(piperazin-1-yl)-quinoline Form A polymorph.
Figure 2:
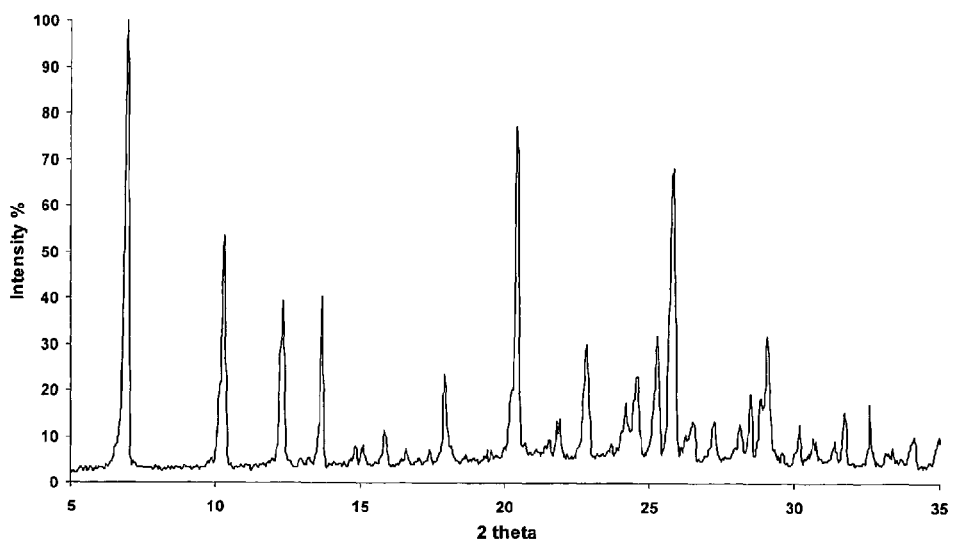
FIG. 2: represents the X-ray spectra of 7-chloro-4-(piperazin-1-yl)-quinoline Form B polymorph.
Figure 3:
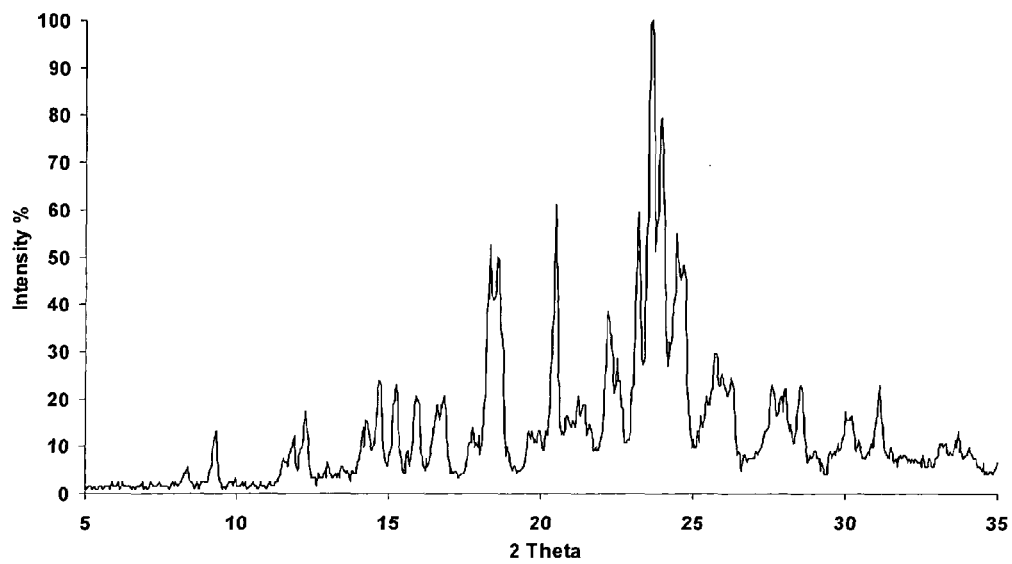
FIG. 3: represents the X-ray spectra of 7-chloro-4-(piperazin-1-yl)-quinoline Form C polymorph.
Figure 4:
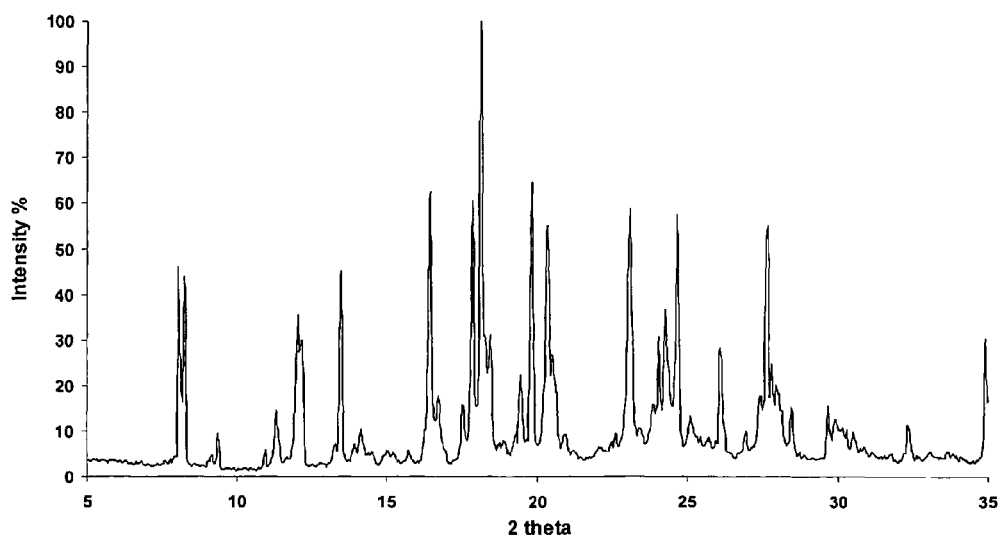
FIG. 4: represents the X-ray spectra of 7-chloro-4-(piperazin-1-yl)-quinoline Form D polymorph.
Figure 5:
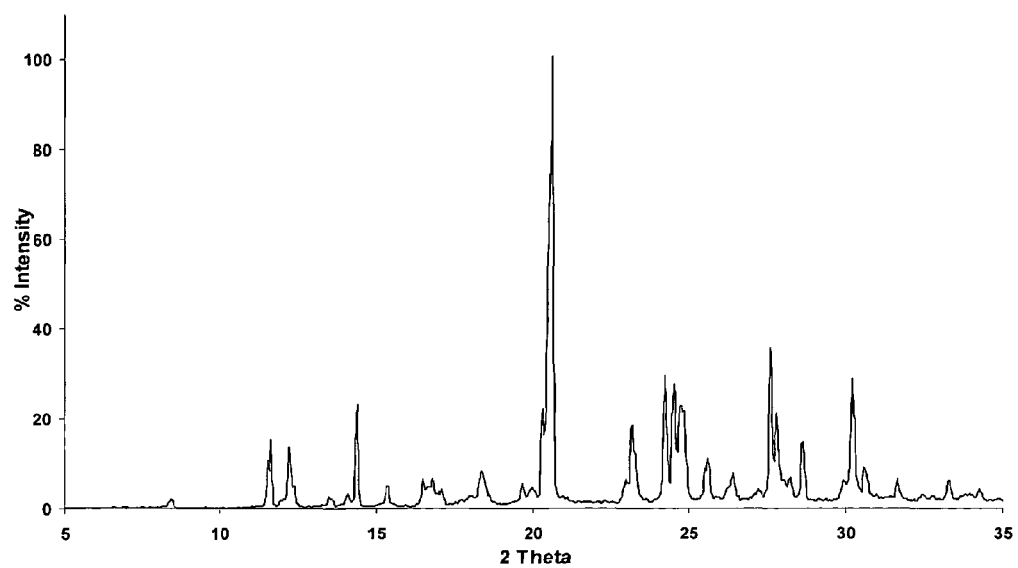
FIG. 5: represents the X-ray spectra of 7-chloro-4-(piperazin-1-yl)-quinoline Form E polymorph.

Abbreviations bs: broad singlet
d: doublet
$CH_2Cl_2$: dichloromethane
$Et_2O$: diethyl ether
RT: room temperature
General Remarks:

Nuclear magnetic resonance ($^1H$ and $^{13}C$ NMR) spectra was gathered, with a Varian Inova 500 spectrometer, and chemical shifts are given in part per million (ppm) downfield from tetramethylsilane as internal standard. The coupling constants are given in Hz.

Example 1

An anhydrous solution of piperazine (54 kg) in 150 l of methanol was stirred until a clear solution was obtained. 50 kg 4,7-dichloroquinoline were then slowly added to the solution. The latter was refluxed for 8 hours and cooled to RT. The resulting suspension was filtered and the solvent removed under reduced pressure. The oil obtained was washed with water (150 l) until solid precipitation occurred. The precipitate was filtered and washed with water to yield 72 kg of crystalline 7-chloro-4-(piperazin-1-yl)-quinoline Form B, containing 25% of water (w/w).

Yield=86% (calculated on dry material).

$^1H$ NMR (200 MHz $CDCl_3$), δ: 1.92 (bs, 1H); 3.16 (s, 8H); 6.81 (d, J=5.1 Hz, 1H); 7.40 (dd, J=2.2 Hz, J=9.0 Hz, 1H); 7.94 (d, J=9.0 Hz, 1H); 8.02 (d, J=2.2 Hz, 1H); 8.58 (d, J=5.1 Hz, 1H).

Purity

The content of piperazine starting material still potentially remaining was assessed by means of gas chromatography analysis.

Gas Chromatographic Conditions:

Column: CAM (J&W) 30 m.×0.25 mm. 0.25 μm film thickness—Stationary phase: base deactivated polyethyleneglycol
Injector: Split/Splitless
Split Ratio: 1:20
Inj Temp: 320° C.
Inj Volume: 1 μl
Column Temp: 100° C. for 3 minutes (10° C./min) to 140° C. per 1 minute
Carrier Flow: 1 ml/min (He)
Detector: FID
Det Temp: 320° C.
Preparation of Example 1 Sample Solution:
50 mg of 7-chloro-4-(piperazin-1-yl)-quinoline prepared according to the procedure described in example 1 was dissolved in 10 ml of ethyl acetate.
Preparation of Piperazine Standard Solution:
100 mg of piperazine (Sigma-Aldrich—Cat. No. P4,590-7) was dissolved in 10 ml of ethyl acetate to obtain a first solution. 50 μl of the latter was diluted to 10 ml with ethyl acetate. This operation was repeated one more time to get the standard solution.

Analysis 1 ml of each of the above solution was analyzed by gas chromatography using the experimental conditions described herein-above.

Piperazine impurity starting material content was determined to be less than 30 ppm.

X-Ray Characterization

It will be understood by those skilled in the art that the 2-theta values of the X-ray powder diffraction pattern may differ slightly from one machine to another or from one sample to another, and therefore the values mentioned are not to be interpreted as absolute. It will be also understood by those skilled in the art that the general intensities in a X-ray powder diffraction pattern may fluctuate according to the measurement conditions (i.e.: position of reflections can be affected by the precise height at which the sample sits in the diffractometer and the zero calibration of the diffractometer; Jenkins, R., et al., "Introduction to X-Ray Powder Diffractometry", John Wiley & Sons 1996).

Therefore, a still further embodiment of the present invention is directed to a crystal form of 7-chloro-4-(piperazin-1-yl)-quinoline that presents a X-ray powder diffraction pattern substantially the same as the X-ray powder diffraction pattern shown in FIG. 1.

In order to assess the physico-chemical properties differences of 7-chloro-4-(piperazin-1-yl)-quinoline obtained through the process of example 1 and processes known in the art, such reaction conditions have been conducted as exemplified in comparison examples 2 to 7.

Comparison Example 2

This comparison example was synthesized following the procedure described in WO09050734.

A mixture of anhydrous piperazine (25.8 g, 0.30 mol), $K_2CO_3$ (13.8 g, 0.10 mol), and 4,7-dichloroquinoline (19.8 g, 0.10 mol) in i-PrOH (140 ml) was heated to reflux for 18 hours. The reaction mixture was then allowed to return to RT and solvent was removed under reduced pressure. The crude reaction mixture was taken-up in $H_2O/CH_2Cl_2$ (600 ml, 1/1). The organic phase was separated and washed again with $H_2O$ before adjusting the pH to 4-4.5 by addition of 50% aq. AcOH. The aqueous layer was then separated and basified by addition of liquor ammonia before being extracted by means of $CH_2Cl_2$. Solvent was removed under reduced pressure and the residue was triturated in hexane for 1 hour. The solid was filtered off to afford 20.26 g of the desired adduct in 82% yield. Further analysis revealed that the solid was crystalline, with crystalline Form E.

Comparison Example 3

This comparison example was synthesized following the procedure described in Indian patent 639MUM2005.

A mixture of anhydrous piperazine (16.3 g, 189 mmol), and 4,7-dichloroquinoline (12.5 g, 63.1 mmol) in MeOH (62.5 ml) was heated to reflux for 8 hours. The reaction mixture was then cooled to 10° C. The precipitate was filtered off and rinsed with cold MeOH (10 ml at 10° C.). The filtrate was evaporated to dryness under reduced pressure after which it was taken-up in $H_2O/CH_2Cl_2$ (500 ml, 1/1). The organic phase was separated and washed again with $H_2O$ (three times 150 ml) before being evaporated under reduced pressure. The residue was triturated in hexane (50 ml) for 1 hour and filtered off. It was further rinsed with hexane (20 ml) to afford 13.75 g of the desired adduct in 88% yield. Further analysis revealed that the solid was crystalline, with crystalline Form E.

Comparison Example 4

This comparison example was synthesized following the procedure described in WO004002960.

A mixture of anhydrous piperazine (43.1 g, 500 mmol), and 4,7-dichloroquinoline (9.9 g, 50 mmol) in EtOH (200 ml) was heated to reflux for 18 hours. The reaction mixture was then allowed to return to RT and solvent was removed under reduced pressure. The crude reaction mixture was dissolved in AcOEt (350 ml) and the resulting solution was washed with water (once with 250 ml and 4 times with 150 ml). The organic phase was then evaporated under reduced pressure to give 11.33 g of the desired adduct in 91% yield. Further analysis revealed that the solid was crystalline, with crystalline Form A.

Comparison Example 5

This comparison example was synthesized following the procedure described by Singh T., et al., in *J. Med. Chem.*, 1971, 14, 4, 283). Further analysis revealed that the solid was crystalline, with crystalline Form E.

Comparison Example 6

This comparison example was synthesized following the procedure described in U.S. Ser. No. 11/420,400 which corresponds to patent application US2006/270852. Further analysis revealed that the solid was crystalline, with crystalline Form E.

Comparison Example 7

The crystalline solid obtained in example 1 was dried in a dessicator at RT in the presence of silica gel for 24 hours to obtain crystalline 7-chloro-4-(piperazin-1-yl)-quinoline Form A.

Example 8

The crystalline solid obtained in example 7 was solved in hot hexane and the resulting solution allowed to cool back to RT. Upon cooling, a further crystalline Form of 7-chloro-4-(piperazin-1-yl)-quinoline, Form C, was obtained.

Example 9

The crystalline solid obtained in example 7 was solved in CH$_2$Cl$_2$ at RT. Upon concentration under reduced pressure, a further crystalline Form of 7-chloro-4-(piperazin-1-yl)-quinoline, Form D, was obtained.

The invention claimed is:

1. A process for the preparation of crystalline polymorph type B of 7-chloro-4-(piperazin-1-yl)-quinoline, the process comprising:
   a) reacting 4,7-dichloroquinoline with anhydrous piperazine in a polar protic solvent for a time of between 6 and 10 hours at reflux temperature to give a suspension;
   b) filtrating the suspension obtained from a);
   c) removing the solvent under reduced pressure and washing the oil thus obtained until crystallization occurs; and
   d) washing the crystals obtained from c), to give the crystalline polymorph type B of 7-chloro-4-(piperazin-1-yl)-quinoline which has a X-ray powder diffraction pattern with at least five specific peaks at about 2-theta=6.95°, 20.40°, 25.80°, 10.30° and 13.70° wherein said values may be plus or minus 0.1° 2-theta and have an intensity of at least 30%,
   wherein the number of equivalents of anhydrous piperazine is less than 3 times the amount of 4,7-dichloroquinoline, and
   the crystalline polymorph type B of 7-chloro-4-(piperazin-1-yl)-quinoline has a purity equal to or higher than 99%.

2. The process according to claim 1, in which the number of equivalents of piperazine is 2.5 times the amount of 4,7-dichloroquinoline.

3. The process according to claim 1, in which the polar protic solvent of a) is MeOH.

4. A crystalline polymorph of type B of 7-chloro-4-(piperazin-1-yl)-quinoline which has a X-ray powder diffraction pattern with at least five specific peaks at about 2-theta=6.95°, 20.40°, 25.80°, 10.30° and 13.70° wherein said values may be plus or minus 0.1° 2-theta and have an intensity of at least 30%, and further shows the following peaks at about 2-theta=12.35°, 25.25°, 29.05°, 22.85°, 17.9°, 24.6°, 28.5° and 28.85° wherein said values may be plus or minus 0.1° 2-theta.

5. The process of claim 1 further comprising:
   a) dissolving the crystals obtained from d) of claim 1 in hot hexane to give a solution;
   b) allowing the solution from a) to cool back to room temperature to enable crystallization; and
   c) filtrating the crystals obtained from b) to give a crystalline polymorph of type C of 7-chloro-4-(piperazin-1-yl)-quinoline which has a X-ray powder diffraction pattern with at least nine specific peaks at about 2-theta=23.6°, 23.95°, 20.4°, 23.2°, 24.45°, 18.3°, 18.6°, 24.7°, and 22.2° wherein said values may be plus or minus 0.1° 2-theta and have an intensity of at least 30%.

6. A crystalline polymorph of type C of 7-chloro-4-(piperazin-1-yl)-quinoline which has a X-ray powder diffraction pattern with at least nine specific peaks at about 2-theta=23.6°, 23.95°, 20.4°, 23.2°, 24.45°, 18.3°, 18.6°, 24.7°, and 22.2° wherein said values may be plus or minus 0.1° 2-theta and have an intensity of at least 30%, and that further shows the following peaks at about 2-theta=25.75°, 22.5°, 26.3°, 14.75°, 15.25°, 27.6°, 28.55°, 31.1°, and 28.05° wherein said values may be plus or minus 0.1° 2-theta.

7. The process of claim 1 further comprising:
   a) dissolving the crystals obtained from d) of claim 1 in dichloromethane to give a solution; and
   b) concentrating the solution from a) under reduced pressure to give a crystalline polymorph of type D of 7-chloro-4-(piperazin-1-yl)-quinoline which has a X-ray powder diffraction pattern with at least eight specific peaks at about 2-theta=18.1°, 19.8°, 16.45°, 17.85°, 23.1°, 24.65°, 20.35°, and 27.65° wherein said values may be plus or minus 0.1° 2-theta and have an intensity of at least 30%.

8. A crystalline polymorph of type D of 7-chloro-4-(piperazin-1-yl)-quinoline which has a X-ray powder diffraction pattern with at least eight specific peaks at about 2-theta=18.1°, 19.8°, 16.45°, 17.85°, 23.1°, 24.65°, 20.35°, and 27.65° wherein said values may be plus or minus 0.1° 2-theta and have an intensity of at least 30%, and that further shows the following peaks at about 2-theta=8.05°, 13.5°, 8.25°, 24.25°, 12.05°, and 24.05° wherein said values may be plus or minus 0.1° 2-theta.

* * * * *